(12) United States Patent
Bergner et al.

(10) Patent No.: US 7,794,082 B2
(45) Date of Patent: Sep. 14, 2010

(54) OPHTHALMOLOGICAL MEASURING SYSTEM AND METHOD FOR DETERMINING THE BIOMETRIC DATA OF AN EYE

(75) Inventors: Roland Bergner, Jena (DE); Ingo Koschmieder, Jena (DE); Wilfried Bissmann, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 33 days.

(21) Appl. No.: 12/096,343

(22) PCT Filed: Dec. 1, 2006

(86) PCT No.: PCT/EP2006/011537

§ 371 (c)(1),
(2), (4) Date: Jun. 5, 2008

(87) PCT Pub. No.: WO2007/079835

PCT Pub. Date: Jul. 19, 2007

(65) Prior Publication Data

US 2008/0278684 A1 Nov. 13, 2008

(30) Foreign Application Priority Data

Dec. 22, 2005 (DE) .................. 10 2005 062 238

(51) Int. Cl.
*A61B 3/10* (2006.01)
*A61B 3/00* (2006.01)
*A61B 8/00* (2006.01)

(52) U.S. Cl. .................. 351/205; 351/206; 351/246; 600/452

(58) Field of Classification Search .................. 351/205, 351/200, 206, 246; 600/300, 407, 437, 449, 600/452
See application file for complete search history.

(56) References Cited

U.S. PATENT DOCUMENTS 6,095,648 A 8/2000 Birngruber et al.

(Continued)

FOREIGN PATENT DOCUMENTS

DE 42 35 079 C2 4/1994

(Continued)

OTHER PUBLICATIONS

Schmid, Gregor F., "Axial and peripheral eye length measured with optical low coherence reflectometry," *J. Biomedical Optics*, vol. 8, No. 4, pp. 655-662 (2003).

*Primary Examiner*—Jack Dinh
(74) *Attorney, Agent, or Firm*—Patterson Thuente Christensen Pedersen, P.A.

(57) ABSTRACT

An ophthalmological measuring system for obtaining biometric data of an eye. with a view to the pre-operative determination of a replacement lens or supplementary lens or refractive operations. The invention includes a combination of a measuring instrument based on ultrasound, an optical measuring instrument, and an evaluation unit, measuring values of the optical measuring instrument and/or of the measuring instrument based on ultrasound being used by the evaluation unit for determining the biometric data of an eye. Furthermore, keratometric and/or pachymetric measurements can also be carried out. The combination of different measuring systems enables a complete examination or diagnosis of a patient on a measuring table, so that the patient does not need to be moved, or have to come back at a later date for more measurements.

14 Claims, 2 Drawing Sheets

U.S. PATENT DOCUMENTS

| | | |
|---|---|---|
| RE37,196 E | 5/2001 | van Gelderen |
| 6,634,751 B2 | 10/2003 | Turner et al. |
| 2002/0077797 A1* | 6/2002 | Hall ............................ 703/11 |
| 2003/0020922 A1 | 1/2003 | Crowley et al. |
| 2003/0214628 A1* | 11/2003 | Patel .......................... 351/200 |
| 2004/0189934 A1 | 9/2004 | Niven |
| 2005/0007551 A1 | 1/2005 | Wakil et al. |
| 2007/0013918 A1 | 1/2007 | Hauger et al. |
| 2007/0088206 A1* | 4/2007 | Peyman et al. .............. 600/319 |
| 2007/0260157 A1* | 11/2007 | Norrby ....................... 600/558 |

FOREIGN PATENT DOCUMENTS

| | | |
|---|---|---|
| DE | 198 12 297 C2 | 9/1999 |
| DE | 103 60 570 A1 | 7/2005 |
| WO | WO 2004/071286 A1 | 8/2004 |
| WO | WO 2004/084719 A1 | 10/2004 |

* cited by examiner

OPHTHALMOLOGICAL MEASURING SYSTEM AND METHOD FOR DETERMINING THE BIOMETRIC DATA OF AN EYE

The present application is a National Phase entry of PCT Application No. PCT/EP2006/011537, filed Dec. 1, 2006, which claims priority from German Application Number 102005062238.0, filed Dec. 22, 2005, the disclosures of which are hereby incorporated by reference herein in their entirety.

FIELD OF THE INVENTION

The invention at hand concerns an opthalmologic measuring system for determining the biometric data of an eye.

BACKGROUND OF THE INVENTION

A number of known methods and measuring instruments exist for determining the biometric data of an eye. For example, it is necessary to determine various biometric parameters of the eye prior to an operation to replace the lens of the eye if there is a clouding of the lens (cataract). To guarantee the optimal post-procedural visual acuity, these parameters must be determined with great accuracy. The appropriate replacement lens is selected based upon established formulae and calculation methods.

The most important parameters to be determined are, among others, the axial length (distance to the retina), the curvature and power of refraction of the cornea as well as the length of the anterior chamber (distance to the eye lens). These measurements can be determined successively using various opthalmologic devices or with the help of specially optimized biometric measuring systems.

For the determination of these parameters primarily ultrasound measuring devices and optical measuring devices based upon short coherence-light procedures prevailed.

With the ultrasound devices there are two different designs that function either based upon the "A-scan" principle or upon the "B-scan" principle. While the A-scan provides only one measurement in the axial direction, there is an additional measurement in transverse direction with the B-scan. The ultrasound procedure basically requires direct contact with the eye.

In this context a device for examining the eye, especially the human eye, is described in DE 42 35079 C2 that basically has the shape of a truncated cone in a shape matched to the eye which contains a probe for the evaluation of acoustic (ultrasound) signals. The probe is affixed at an oblique angle to the central axis of the holder and is suitable for transmitting as well as for receiving pulsed signals.

The specific disadvantages of the determination of the biometric data of an eye using ultrasound devices are, on one hand, the lesser accuracy and, on the other hand, the requirement of direct contact with the eye. This way the measurements could be distorted through denting of the eyeball. These disadvantages can be reduced through the use of the immersion technique where ultrasound waves are directed at the eye through a funnel filled with water and placed over the eye, but the major disadvantages of this measuring method remain.

These lie, on one hand, in the necessity of direct contact with the eye which always carries the risk of transmission of infections and, on the other hand, it is necessary to anesthetize the eye for the determination of the data. For the correct selection of the replacement lens it must be ascertained that the visual axis of the eye is appropriately aligned when determining the biometric data. For this purpose special devices must be provided for the ultrasound equipment since the alignment of the visual axis does not happen automatically.

Analogous to the ultrasound devices, where images of the structural transitions can be reconstructed based upon the acoustic signals, optical images of the structural transitions are depicted as two-dimensional depth tomograms. In this regard the OCT procedure (OCT=optical coherence tomography) has prevailed as a short coherence-light procedure where temporal incoherent light is used with the help of an interferometer for measuring the distance of reflective and dispersive materials.

The underlying principle of the OCT procedure is based upon white light interferometry and compares the travel time of a signal using an interferometer (in most cases a Michelson interferometer). The arm with a known optical length (=reference arm) is used as a reference arm for the measuring arm. The interference of the signals from both arms yields a pattern from which one can determine the relative optical travel distance within an A-scan (individual depth signal). In the one-dimensional scanning grid procedure the beam is guided transversally in one or two directions, analogous to the ultrasound technique, allowing the recording of a plane B-scan or a three-dimensional tomogram (C-scan). This way, the amplitude data of the individual A-scans are depicted as logarithmized gray scale or phantom color data. For example, a measuring time of one second will be needed for a B-scan consisting of 100 individual A-scans.

The measuring resolution of the OCT procedure is determined by the coherency length of the light source used and is typically about 15 µm. Due to its special suitability for examining optically transparent media the procedure is widespread in the field of opthalmology.

Two different kinds of OCT procedures have prevailed among those used in the field of opthalmology. With the first kind, the reference arm is modified in length to determine the measured data and continually measure the intensity of the interference without consideration given to the spectrum. This procedure is called "Time Domain" procedure. With the other procedure, called "Frequency Domain" procedure, however, the spectrum is considered in determining the measurements and the interference of the individual spectral components are recorded. Therefore, we refer to a signal within the time domain, on one hand, and to a signal within the frequency domain on the other.

The advantage of the frequency domain lies in the simple and quick simultaneous measuring where complete information about the depth can be determined without requiring movable parts. This increases both the stability and the speed.

The big technological advantage of the OCT is the decoupling of the depth resolution from the transversal resolution. In contrast to microscopy, this allows the recording of the three-dimensional structure of the item to be examined. The purely reflective and, therefore, contact-free measuring makes it possible to generate microscopic images of live tissue (in vivo).

Due to the high selectivity of the method very weak signals (less than a nanowatt) can be detected and identified to a certain depth. Therefore, the procedure is suitable for examining optically sensitive tissue. The use of the OCT procedures is limited by the depth penetration of the electromagnetic radiation into the subject to be examined, which is dependent upon the wavelength, as well as by the resolution, which depends upon the bandwidth.

With the currently customary biometric measuring devices, the measured data are processed in the device and suggestions are made as to the exchange lenses to be used.

These depend upon the formulae used in the calculation and the type of available lenses (depending on the manufacturer). It is possible, or necessary, to let the post-operative results enter into the calculation formulae via the optimization of constants in order to allow for individual influences during the surgery as well as the measuring technique actually used. All measured values, data, and formulae are administered, analyzed, and saved in data banks and software programs. In part, these solutions are integrated in networks and various additional applications can be linked to them.

With the optical measuring devices based upon short coherence-light procedures, the interferometric principle based upon the dual-beam is used. This procedure is contact-free and works with the greatest accuracy currently possible. Solutions based upon this measuring principle have been described as examples in DE 198 12 297 C2, DE 103 60 570 A1 and WO 2004/071286 A1.

The disadvantages pointed out with the ultrasound devices can be avoided with the optical procedure. Special mention should be made of the high degree of accuracy (interferometer) and patient comfort. However, the disadvantage here is the fact that 10 to 20 percent of patients cannot be measured because, for example, the scattering of dense cataracts attenuates the measuring signal too much and the laser output cannot be increased at will due to the limits to be respected around the eye. In these cases it is also possible that the patient is no longer able to see the focal point and measuring becomes difficult.

Certain pathological changes can cause individual problems with determining the measuring data with both procedures. As a result of these negative influences upon obtaining the measurements there is an increased risk of making the wrong decision when selecting a suitable exchange lens.

SUMMARY OF THE INVENTION

The invention at hand is based upon the task of developing a solution which avoids the disadvantages of the current state of technology and makes it possible to determine biometric measuring data of an eye even under difficult conditions with great reliability and accuracy.

The present technical solution is intended to determine the biometric data of an eye within the scope of the pre-operative determination of the exchange lens, or additional lens, or refractive procedures, where measuring data can be determined even under difficult circumstances with great reliability and accuracy. In addition, the proposed solution allows the determination of the position of the anterior chamber and lens of the eye, the shape of the front of the cornea of the human eye (keratometric measurement), as well as the thickness of the cornea (pachymetric measurement).

BRIEF DESCRIPTION OF THE DRAWINGS

The invention is described below in more detail through embodiments. The following figures will show.

DETAILED DESCRIPTION

The opthalmologic measuring system for determining the biometric data of an eye, according to the invention, within the scope of the pre-operative determination of the exchange lens, or additional lens, or refractive procedure, includes a combination of a measuring device that is based upon ultrasound plus an optical measuring device and an evaluating device. The evaluation unit uses measuring data from the optical and/or the ultrasound measuring device to determine the biometric data of an eye.

The optical measuring device used here can be a Scheimpflug camera or an optical measuring device based upon short coherence-light procedures such as, for example, an IOLMaster® (Carl Zeiss Meditec AG).

While a Scheimpflug camera can be used to generate 2-dimensional images of the front parts of the eye and to measure distances in this area of the eye, the IOLMaster® is used for the exact determination of the axial length, the anterior chamber of the eye, and the power of refraction of the cornea.

In an advantageous technical embodiment the measuring data obtained by the evaluating unit of both measuring devices are used for mutual calibration where preferably sample eyes are used. The data transmission required for this is accomplished preferably via a data link that connects the evaluating units of both measuring devices.

In another technical embodiment both measuring devices are integrated into one device which will make the opthalmologic measuring device more compact and easier to handle. This offers the additional advantage that certain systems components, such as PC, monitor, as well as input and output units can be used jointly.

Figure 1:
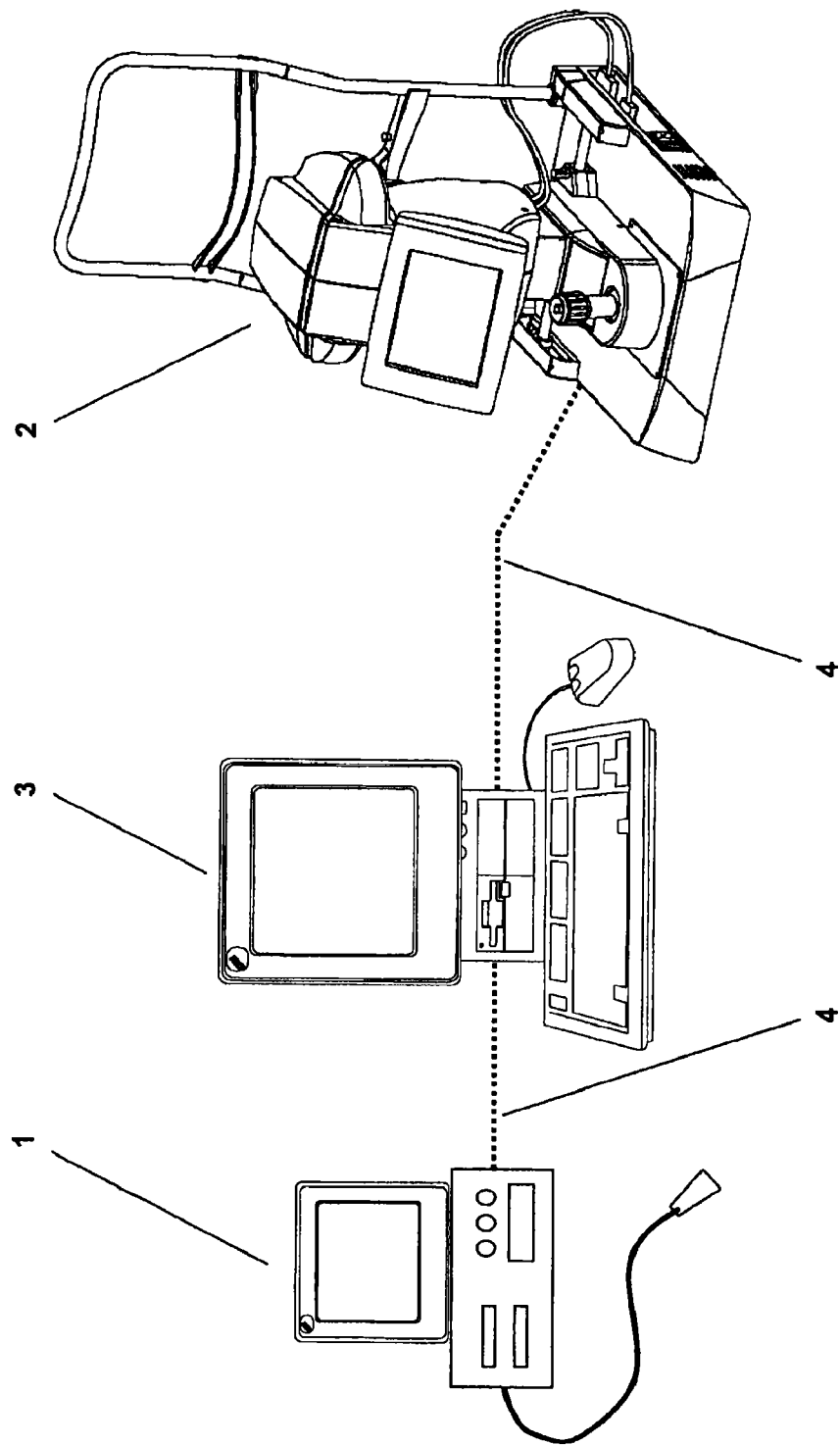
FIG. 1: an opthalmologic measuring system as a coupling of an optical measuring device based upon ultrasound and one based upon a short coherence-light process

The combination of a measuring device 1, based upon ultrasound shown in FIG. 1 (acoustic image generating procedure to depict the front and/or back areas of the eye), and an optical measuring device 2 based upon short coherence-light procedures (optical image generating procedure to depict the front and/or back areas of the eye), represents a particularly advantageous opthalmologic measuring system where, preferably, an IOLMaster® by the Carl Zeiss Meditec AG company is used as measuring device 2. This opthalmologic measuring system allows for a comprehensive examination or the clarification of unanticipated or unclear results. Preferably the evaluating unit 3 uses the measured data to provide and evaluate 2-dimensional or 3-dimensional images of the examined eye. The transmission of the measuring data required for this is handled via the data transmission line 4 which connects the evaluating unit 3 with the two measuring devices 1 and 2.

Figure 2:
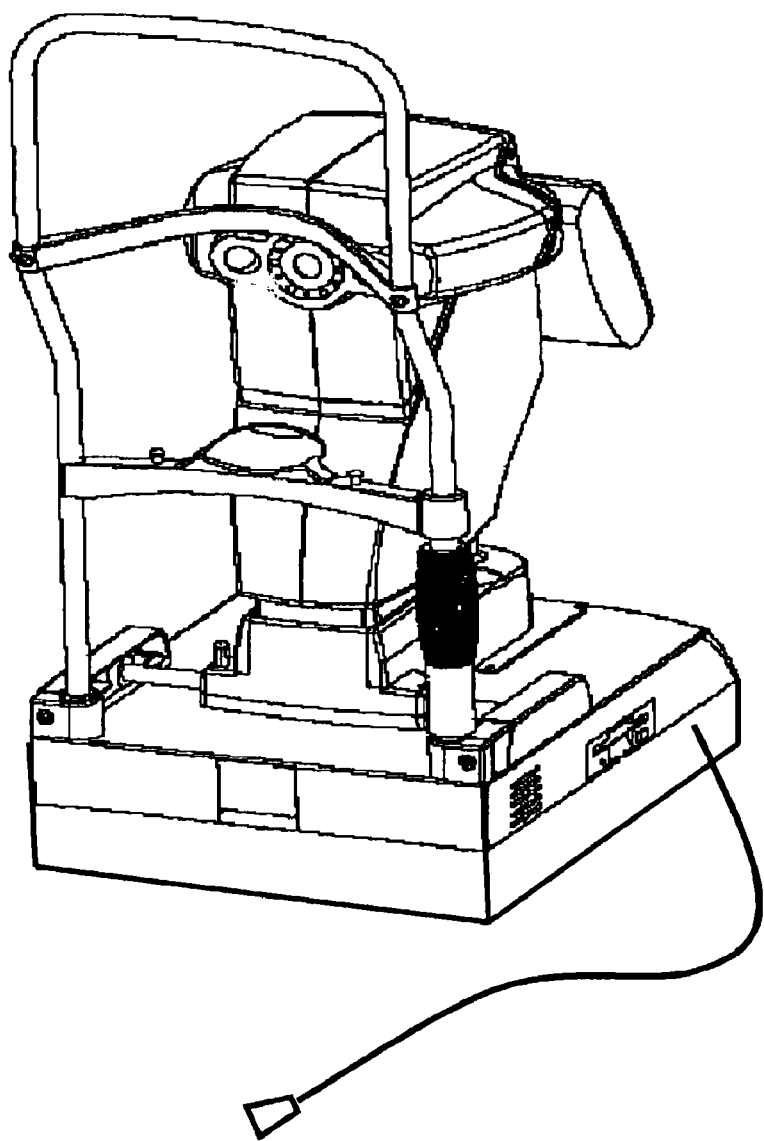
FIG. 2: an opthalmologic measuring system where an optical measuring device based upon ultrasound and one based on short coherence-light process are integrated.

By contrast, FIG. 2 shows an opthalmologic measuring system where an optical measuring device based upon ultrasound and one based upon short coherence-light procedures are integrated.

The biometric data of an eye determined by the opthalmologic measuring system can be passed on in an advantageous manner within the scope of the pre-operative determination of the exchange, or additional lens, or refractive procedures, to post-procedural devices, such as e.g. surgical microscopes.

With this procedure according to the invention for the pre-operative determination of the exchange, or additional lens, or refractive procedures, measuring data from a measuring device based upon ultrasound and/or an optical device will be supplied to an evaluating unit where they are used by the evaluating unit to determine the parameters of the lens to be implanted, using known formulae and calculation methods.

The biometric data generated by the evaluating unit, based upon measuring data determined by both measuring devices, will be compared with each other. This offers the advantage that possible erroneous measurements can be detected and corrected. In case there are significant differences between the measured data of the two measuring devices, it always makes sense to produce a 2-dimensional image of the eye in order to be able to find the cause of the faulty measuring results. Possible reasons for such differences could be retinal detachment or staphyloma. Also, in pseudophakic eyes, artefacts could appear in the various measuring procedures that could lead to faulty measuring results if interpreted incorrectly.

Besides, it is an advantage for increasing the reliability and accuracy to use the measuring data of both measuring devices for mutual calibration preferably using sample eyes. The measuring data obtained by both measuring devices can also be used to optimize the lens constants.

In yet another embodiment of the procedure, the measuring data of two separate measuring devices are further processed by the evaluating unit of the respective measuring device and the results are then handed off to the other measuring device via a data link.

With the solution according to the invention, an opthalmologic measuring system and a process to determine the biometric data of an eye is being provided which can determine measuring data with great reliability and accuracy, even under difficult circumstances.

The combination makes it possible to compensate for the given specific disadvantages of the various measuring procedures, at least in part, without losing their advantages. The very high accuracy of the optical measuring procedure with the corresponding contact-free determination of measuring data is preserved as well as the option to use ultrasound-based measuring procedures under difficult circumstances, such as a dense cataract. A comparison of the measured data from the two systems can further enhance the reliability and accuracy of the measuring data.

The combination of different measuring procedures allows a complete examination and assessment of the patient at one single measuring position so that the patient neither has to be moved nor must additional measuring appointments be scheduled on another day.

Determining a multitude of different biometric data of an eye allows for an improved characterization of the patient's eyesight and makes the selection of replacement or refractive additional lenses more reliable.

The invention claimed is:

1. An ophthalmologic measuring system to determine the biometric data of an eye within the scope of pre-operative selection of an intraocular lens for lens exchange, implantation of an additional intraocular lens, or planning a refractive surgical procedure, comprising:
    an ultrasound-based measuring device;
    an optical measuring device that determines axial lengths of the eye; and
    an evaluating unit operably coupled to the ultrasound-based measuring device and the optical measuring device, wherein the evaluating unit uses measuring data from the optical measuring device and from the ultrasound-based measuring device to determine the biometric data of an eye.

2. The ophthalmologic measuring system according to claim 1, wherein the optical measuring device is an optical measuring device based on a short coherence-light procedure.

3. The ophthalmologic measuring system according to claim 1, wherein the optical measuring device comprises a Scheimpflug camera.

4. The ophthalmologic measuring system according to claim 1, wherein the optical measuring device based upon a short coherence-light procedure comprises an IOLMaster® instrument.

5. The ophthalmologic measuring system according to claim 1, wherein the evaluating unit uses the measuring data obtained from the ultrasound-based measuring device and the optical measuring device for mutual calibration of the ultrasound-based measuring device and the optical measuring device and further wherein the measuring data are acquired by measuring sample eyes.

6. The ophthalmologic measuring system according to claim 1, wherein the measuring system is configured as a workstation comprising the ultrasound-based measuring device and the optical measuring device, and further wherein the measuring data are passed on via a data link.

7. The ophthalmologic measuring system according to claim 1, where the ultrasound-based measuring device and the optical measuring device are integrated into one device.

8. The ophthalmologic measuring system according to claim 1, further comprising connections and/or data links to another device.

9. The ophthalmologic measuring system according to claim 1, wherein the measuring data is received from both the ultrasound-based measuring device and the optical measuring device and processed by the evaluating unit to create processed data; and
    the processed data is transferred via a data link such that the processed data from the ultrasound-based measuring device is transferred to the optical measuring device and the processed data from the optical measuring device is transferred to the ultrasound-based measuring device.

10. An ophthalmologic measuring method to determine the biometric data of an eye within the scope of pre-operative selection of an intraocular lens for lens exchange, implantation of an additional intraocular lens, or refractive surgical procedure, comprising:
    operably coupling an ultrasound-based measuring device, an optical measuring device that determines axial lengths of the eye and an evaluating unit
    receiving measuring data from the ultrasound-based measuring device and from the optical measuring device at the evaluating unit; and
    determining parameters of an intraocular lens to be implanted based upon known formulae and calculation methods via the evaluating unit.

11. The method according to claim 10, further comprising:
    supplying measuring data from both the ultrasound-based measuring device and the optical measuring device to the evaluating unit;
    determining the parameters of the lens to be implanted via the evaluating unit based on the known formulae and calculating methods from the data from the ultrasound-based measuring device to determine a first result;
    determining the parameters of the lens to be implanted via the evaluating unit based upon the known formulae and calculating methods from the data from the optical measuring device to determine a second result; and
    comparing the first result with the second result.

12. The method according to claim 10, further comprising utilizing the measuring data obtained from the ultrasound-based measuring device and the optical measuring device for mutual calibration of the ultrasound-based measuring device and the optical measuring device and acquiring the measuring data by measuring sample eyes.

13. The method according to claim 10, further comprising obtaining the measuring data from both the ultrasound-based measuring device and the optical measuring device; and
    using the measuring data for optimization of lens constants.

14. The method according to claim 10, further comprising receiving measuring data from both the ultrasound-based measuring device and the optical measuring device at the evaluating unit;

processing the measuring data with the evaluating unit to create processed data; and transferring the processed data via a data link such that the processed data from the ultrasound-based measuring device is transferred to the optical measuring device and the processed data from the optical measuring device is transferred to the ultrasound-based measuring device.

* * * * *

UNITED STATES PATENT AND TRADEMARK OFFICE
CERTIFICATE OF CORRECTION

| | | |
|---|---|---|
| PATENT NO. | : 7,794,082 B2 | Page 1 of 1 |
| APPLICATION NO. | : 12/096343 | |
| DATED | : September 14, 2010 | |
| INVENTOR(S) | : Bergner et al. | |

It is certified that error appears in the above-identified patent and that said Letters Patent is hereby corrected as shown below:

On the Title page, Item (57), line 2, in the Abstract. The "." after "data of an eye" should be deleted.

An ophthalmological measuring system for obtaining biometric data of an eye[[.]] with a view to the pre-operative determination of a replacement lens or supplementary lens or refractive operations.

Signed and Sealed this

Eleventh Day of September, 2012

David J. Kappos
*Director of the United States Patent and Trademark Office*